(12) United States Patent
Karabal et al.

(10) Patent No.: US 8,975,430 B2
(45) Date of Patent: Mar. 10, 2015

(54) PHENOLYTIC KINETIC RESOLUTION OF AZIDO AND ALKOXY EPOXIDES

(71) Applicant: Council of Scientific & Industrial Research, New Delhi (IN)

(72) Inventors: Pratibha Uttam Karabal, Pune (IN); Dayanand Ambadas Kamble, Pune (IN); Arumugam Sudalai, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/367,576

(22) PCT Filed: Dec. 20, 2012

(86) PCT No.: PCT/IN2012/000832
§ 371 (c)(1),
(2) Date: Jun. 20, 2014

(87) PCT Pub. No.: WO2013/093943
PCT Pub. Date: Jun. 27, 2013

(65) Prior Publication Data
US 2014/0350276 A1    Nov. 27, 2014

(30) Foreign Application Priority Data

Dec. 20, 2011   (IN) .......................... 3732/DEL/2011

(51) Int. Cl.
C07F 7/10    (2006.01)
C07F 7/08    (2006.01)
C07F 7/18    (2006.01)

(52) U.S. Cl.
CPC .................................. C07F 7/1892 (2013.01)
USPC ........... 556/416; 556/436; 556/441; 556/465; 568/337

(58) Field of Classification Search
USPC ................... 556/465, 416, 436, 441; 568/337
See application file for complete search history.

(56) References Cited

FOREIGN PATENT DOCUMENTS

WO    WO2010042030 A1    4/2010

OTHER PUBLICATIONS

Reddy et al., "Co(III)(salen)-catalyzed HKR of two stereocentered alkoxy- and azido epoxides: a concise enantioselective synthesis of (S,S)-reboxetine and (+)-epi-cytoxazone", Chem Commun (Camb) (2010), 46 (27):5012-5014.
Ready et al., "Highly active oligomeric (salen)co catalysts for asymmetric epoxide ring-opening reactions", J Am Chem Soc (2001), 123(11):2687-8.

*Primary Examiner* — Porfirio Nazario Gonzalez
(74) *Attorney, Agent, or Firm* — Bret E. Field; Bozicevic, Field & Francis LLP

(57) ABSTRACT

Disclosed herein is a single step catalytic process for the production of enantiomerically pure α-Aryloxy-α'-Azido/Alkoxy alcohols of formula (A). The invention, in particular discloses phenolytic kinetic resolution of racemic anti and syn azido/alkoxy epoxides to generate two stereocentres of high optical purities of formula (A).

Formula A

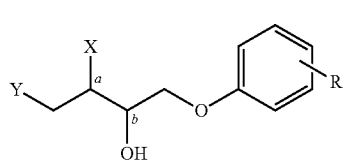

10 Claims, No Drawings

PHENOLYTIC KINETIC RESOLUTION OF AZIDO AND ALKOXY EPOXIDES

The following specifications particularly describe the nature of the invention and the manner in which it is to be performed:

TECHNICAL FIELD OF INVENTION

The present invention relates to a single step catalytic process for the production of enantiomerically pure α-Aryloxy-α'-Azido/Alkoxy alcohols of formula (A). The invention in particular, relates to Phenolytic Kinetic Resolution of racemic anti and syn azido/alkoxy epoxides to generate two stereocentres of high optical purities of formula (A).

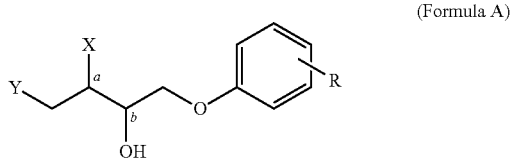

(Formula A)

Wherein X is selected from $N_3$ and OBn;
'R' is selected independently from hydrogen, alkyl ($C_1$-$C_5$), alkenyls ($C_2$-$C_6$), alkynyls ($C_2$-$C_6$), aryl, alkoxy, cyano, halo, nitro, —C(O)—$R_1$, —$CO_2R_2$, hydroxyl, —NH($R_3$), cycloalkyl, cycloalkenyl, thiols, thiocarbonyl, sulfonyl or a heterocycle($C_3$-$C_5$), where $R_1$, $R_2$ and $R_3$ represent hydrogen, alkyl($C_1$-$C_5$).
Y denotes tert-butyldimethylsilyloxide (TBSO) or phenyl; and
'a' and 'b' denote syn or anti position.

BACKGROUND AND PRIOR ART

Enantiopure mono hydroxyl syn or anti azido/alkoxy-1,2-diols are valuable building blocks for the bioactive pharmaceuticals. It is a known fact that enantiomerically pure drugs have numerous advantages over racemic drug mixtures including advantages, such as, fewer side effects and greater potency, which result in part from the ability of living systems to differentiate between enantiomeric compounds. Access to these building blocks is provided by several routes including asymmetric reduction of aryloxy ketones or the ring opening of enantiopure terminal epoxides.

Ring opening of terminal epoxides in presence of a chiral catalyst known in the art are used to resolve single epoxide.

An article titled "Asymmetric Processes Catalyzed by Chiral (Salen) Metal Complexes" by Jay F. Larrow and Eric N. Jacobsen in Topics Organomet Chem (2004) 6: 123-152 relate to catalytic asymmetric ring opening or kinetic resolution of meso and racemic terminal epoxides using variety of synthetically useful nucleophiles to obtain enantiopure dissymmetrically substituted epoxides. The catalyst is selected from chiral (salen)Co(III) and Cr(III) complexes. An article titled "Asymmetric Catalytic Synthesis of α-Aryloxy Alcohols: Kinetic Resolution of Terminal Epoxides via Highly Enantioselective Ring-Opening with Phenols by Joseph M. Ready and Eric N. Jacobsen in J. Am. Chem. Soc. 1999,121, 6086-6087 relates to phenolytic kinetic resolution of terminal epoxides in presence of (salen)Co(III) catalyst to generate 1-aryloxy-2-alcohols.

The aforementioned kinetic resolution technique, however, results in α-aryloxy alcohol with only one stereo centre.

Further, the processes described in the art to synthesize functionalized α-Aryloxy alcohols involve higher temperature conditions and protection/deprotection of various functional groups leading to multistep reaction sequences thereby limiting the overall yield and the enantioselectivity of the process particularly unsuitable for the atom economic synthesis.

In context with the growing demand for enantiopure α-azido/alkoxy alcohols as intermediate in preparation of enantiomeric pure drugs and to expand the scope of stereoselective ring opening of racemic terminal epoxides, present inventors have explored the possibility of improving upon the existing kinetic resolution technique to provide enantiopure α-Aryloxy-α'-Azido/Alkoxy alcohols with two stereocentres.

The previous work published by the applicant in the article titled "Co(III)(salen)-catalyzed HKR of two stereocentered alkoxy- and azido epoxides: a concise enantioselective synthesis of (S,S)-reboxetine and (+)-epi-cytoxazone" by R. Santhosh Reddy, Pandurang V. Chouthaiwale et. al in Chem. Commun., 2010, 46, 5012-5014 discloses hydrolytic kinetic resolution (HKR) of racemic syn- or anti- alkoxy- and azido epoxides catalyzed by Co(salen) complex to obtain enantioenriched syn- or anti- alkoxy- and azido epoxides and the corresponding 1,2-diols.

The present inventors have observed that synthesis of certain bioactive molecules is still difficult using the previously known kinetic resolution technique with water as nucleophile. Moreover, selective protection of alcohols is generally tedious which may increase the number of steps in the preparation of bio active products.

In view of the above, there remains a need to provide an economical process that can provide monohydroxy protected syn or anti azido/alkoxy-1,2-diols as valuable "building blocks" for the bioactive pharmaceuticals.

OBJECT OF THE INVENTION

The main objective of the present invention is to provide a single step catalytic process for the production of enantiomerically pure α-Aryloxy-α'-Azido/Alkoxy alcohols of formula (A).

Another objective of the present invention is to provide Phenolytic Kinetic Resolution of racemic anti and syn azido/alkoxy epoxides to generate two stereocentres of high optical purities of formula A.

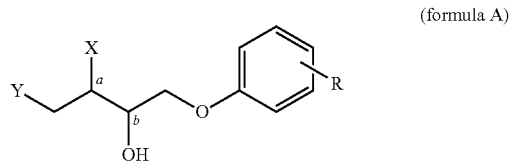

(formula A)

Another objective of the present invention is to provide a process for asymmetric synthesis of antihypertensive agent ICI118,551((2S,3S)-1-(2,3-dihydro-4-methyl-1H-inden-7-yloxy)-3-(isopropylamino)butan-2-ol) from intermediate (17).

SUMMARY OF THE INVENTION

Accordingly, the present invention provides a single step process for the synthesis of α-Aryloxy-α'-Azido/Alkoxy alcohols of general formula A with two stereocenters by phenolytic kinetic resolution,

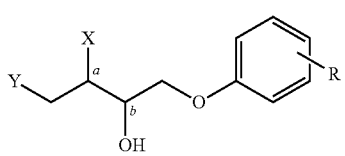

(formula A)

wherein X is selected from N₃ and OBn;
'R' is selected independently from hydrogen, alkyl ($C_1$-$C_5$), alkenyls ($C_2$-$C_6$), alkynyls ($C_2$-C6), aryl, alkoxy, cyano, halo, nitro, —C(O)—$R_1$, —CO₂$R_2$, hydroxyl, —NH($R_3$), cycloalkyl, cycloalkenyl, thiols, thiocarbonyl, sulfonyl or a heterocycle($C_3$-$C_5$), where $R_1$, $R_2$ and $R_3$ represent hydrogen, alkyl($C_1$-$C_5$).
Y denotes TBSO or phenyl; and
'a' and 'b' denote syn or anti position
Wherein the said process comprising the steps of;
(a) adding racemic epoxide of formula (1),

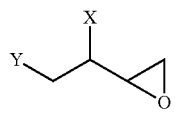

Formula 1 to phenol of formula (2)

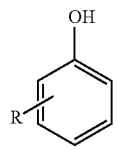

Formula 2 wherein, X, Y and R are as defined above,
at room temperature ranging between 25-35° C. to preformed (salen) Co (III) catalyst of formula 3,

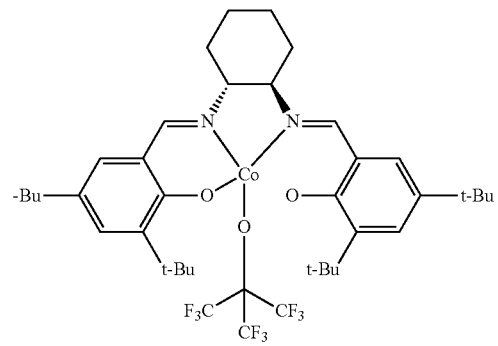

Formula 3

(R,R)-Co salen complex 3 followed by addition of tertiary butyl methyl ether, stirring and adding pyridinium p-toluene sulfonate, filtering, concentrating, followed by purifying to obtain the α-Aryloxy-α'-Azido/Alkoxy alcohols of general formula A.
In an embodiment of the invention, the anti α-Aryloxy-α'-Azido/Alkoxy alcohols, is represented by formula 4;

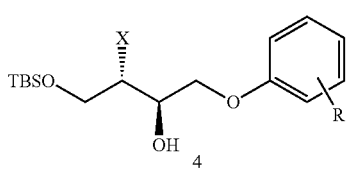

Formula 4

4a: X = N₃ (2S, 3S)
4b: X = OBn (2R, 3S)

In one embodiment of the invention, the syn α-Aryloxy-α'-Azido/Alkoxy alcohols is, represented by formula 7;

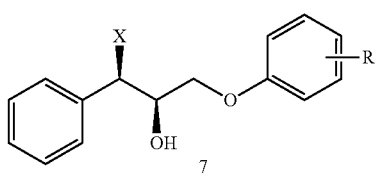

Formula 7

7a: X = N₃ (2S, 3R)
7b: X = OBn (2R, 3R)

In another embodiment of the invention, the α-Aryloxy-α'-Azido/Alkoxy alcohols of formula 4 and 7 comprises;

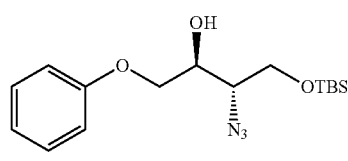 [SMILES: CC(C)(C)[Si](C)(C)OC[C@H](N=[N+]=[N-])[C@H](O)COc1ccccc1]

(2S,3S)-3-azido-4-(tert-butyl-dimethylsiloxy)-1-phenoxybutan-2-ol

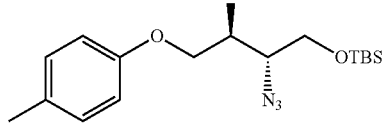

(2S,3S)-1-(p-tolyloxy)-3-azido-4-(tert-butyl-dimethyl siloxy)butan-2-ol

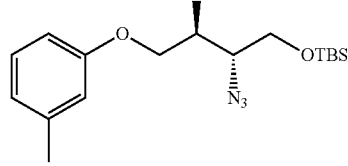

(2S,3S)-1-(m-tolyloxy)-3-azido-4-(tert-butyl-dimethyl siloxy)butan-2-ol

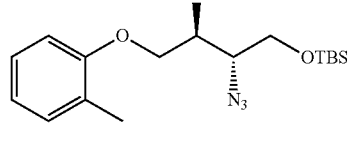

(2S,3S)-1-(o-tolyloxy)-3-azido-4-(tert-butyl-dimethyl siloxy)butan-2-ol (2S,3S)-1-(4-tert-butylphenoxy)-3-azido-4-(tert-butyl-dimethylsiloxy)butan-2-ol (2S,3S)-1-(3-methoxyphenoxy)-3-azido-4-(tert-butyl-dimethylsiloxy)butan-2-ol 4-((2S,3S)-(3-azido-4-(tert-butyl-dimethyl-hydroxybutoxy)benzonitrile (2S,3S)-1-(4-nitrophenoxy)-3-azido-4-(tert-butyl-dimethylsiloxy)butan-2-ol (2S,3S)-1-(4-fluorophenoxy)-3-azido-4-(tert-butyl-dimethylsiloxy)butan-2-ol (2S,3S)-1-(4-bromophenoxy)-3-azido-4-(tert-butyl-dimethyl siloxy)butan-2-ol (2S,3S)-1-(4-chlorophenoxy)-3-azido-4-(tert-butyl-dimethyl siloxy)butan-2-ol (2S,3S)-1-(3,5-dichlorophenoxy)-3-azido-4-tert-butyl-dimethylsiloxy)butan-2-ol 1-(4-(2S,3S)-(3-azido-4-(tert-butyl-dimethyl siloxy)-2-hydroxybutoxy)phenyl)ethanone 4-((2S,3S)-(3-azido-4-tert-butyl-dimethyl siloxy)-2-hydroxybutoxy)benzaldehyde 2-(2S,3S)-(3-azido-4-(tert-butyl-dimethyl siloxy)-2-hydroxybutoxy)-5-bromobenzaldehyde methyl 4-((2S,3S)-(3-azido-4-(tert-butyl-dimethylsiloxy-2-hydroxybutoxy)benzoate (2S,3S)-1-(2,3-dihydro-4-methyl-1H-inden-7-yloxy)-3-azido-4-(tert-butyl-dimethyl siloxy)butan-2-ol 4-((2R,3S)-4-(tert-butyl dimethylsiloxy)-3-(benzyloxy)-2-hydroxybutoxy)benzonitrile

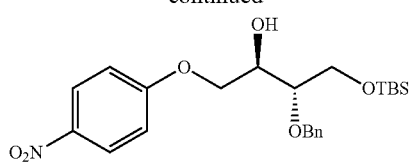

(2R,3S)-4-(tert-butyl dimethylsiloxy)-1-
(4-nitrophenoxy)-3-(benzyloxy)butan-2-ol

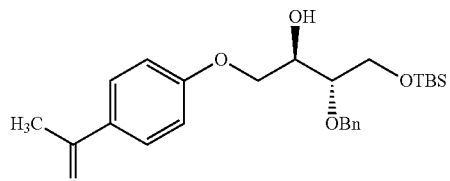

1-(4-((2R,3S)-4-(tert-butyl dimethylsiloxy)-3-
(benzyloxy)-2-hydroxybutoxy)phenyl)ethanone

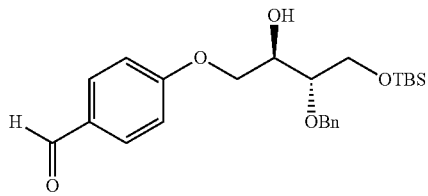 [SMILES: CC(C)(C)[Si](C)(C)OC[C@H](OCc1ccccc1)[C@H](O)COc1ccc(C=O)cc1]

4-((2R,3S)-4-(tert-butyl dimethylsiloxy)-3-
(benzyloxy)-2-hydroxybutoxy)benzaldehyde

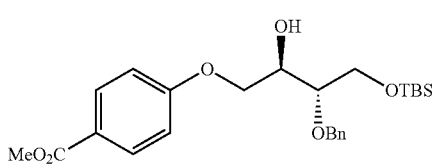 [SMILES: COC(=O)c1ccc(OC[C@@H](O)[C@H](CO[Si](C)(C)C(C)(C)C)OCc2ccccc2)cc1]

methyl 4-((2R,3S)-4-(tert-butyl dimethylsiloxy)-3-
(benzyloxy)-2-hydroxybutoxy)benzoate

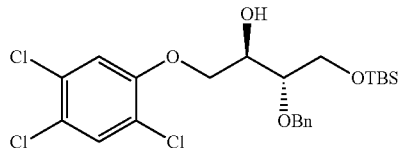 [SMILES: CC(C)(C)[Si](C)(C)OC[C@H](OCc1ccccc1)[C@H](O)COc1cc(Cl)c(Cl)cc1Cl]

(2R,3S)-1-(2,4,5-trichlorophenoxy)-4-
(tert-butyldimethylsiloxy)-3-(benzyloxy)butan-2-ol

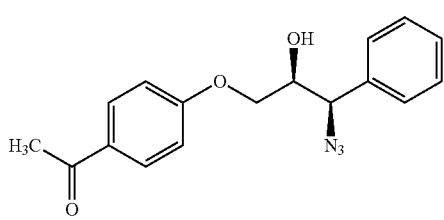 [SMILES: CC(=O)c1ccc(OC[C@@H](O)[C@H](N=[N+]=[N-])c2ccccc2)cc1]

1-(4-((2S,3R)-3-azido-2-hydroxy-3-
phenylpropoxy)phenyl)ethanone

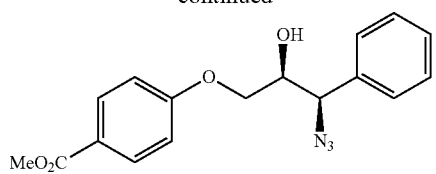

methyl 4-((2S,3R)-3-azido-2-hydroxy-3-
phenylpropoxy)benzoate

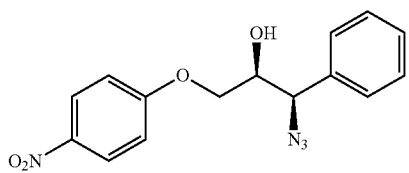 [SMILES: [N-]=[N+]=N[C@H](c1ccccc1)[C@H](O)COc1ccc([N+](=O)[O-])cc1]

(1R,2S)-3-(4-nitrophenoxy)-1-azido-1-
phenylpropan-2-⊘

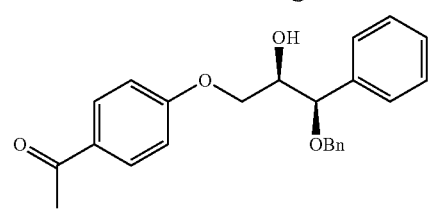

1-(4-((2R,3R)-3-(benzyloxy)-2-hydroxy-3-
phenylpropoxy)phenyl)ethanone

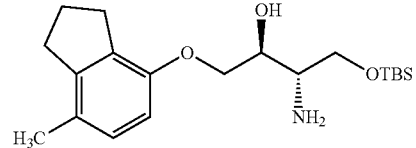

(2S,3S)-1-(2,3-dihydro-4-methyl-1H-inden-7-yloxy)-3-
amino-4-(tert-butyldimethylsiloxy)butan-2-ol

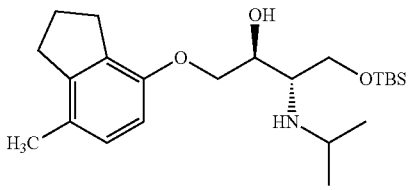

(2S,3S)-1-(2,3-dihydro-4-methyl-1H-inden-7-yloxy)-4-
(tert-butyldimethylsiloxy)-3-(isopropylamino)butan-2-ol

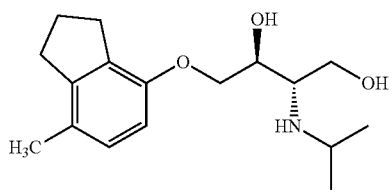

(2S,3S)-4-(2,3-dihydro-4-methyl-1H-inden-7-yloxy)-2-
(isopropylamino)butane-1,3-diol In yet another embodiment, the yield of α-Aryloxy-α'-Azido/Alkoxy alcohols of general formula A is in the range of 35-98%

In still another embodiment, enantiomeric excess (ee) % of α-Aryloxy-α'-Azido/Alkoxy alcohols of general formula A is in the range of 94-99%

In still another embodiment, a process for asymmetric synthesis of antihypertensive agent ICI118,551((2S,3S)-1-(2,3-dihydro-4-methyl-1H-inden-7-yloxy)-3-(isopropylamino)butan-2-ol)

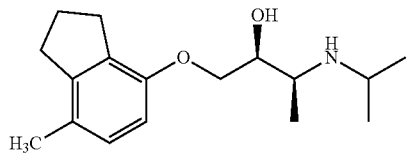

from intermediate (17)

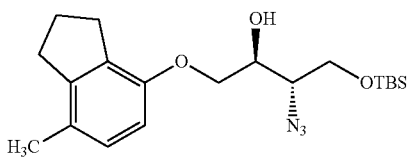

(2S,3S)-1-(2,3-dihydro-4-methyl-1H-inden-7-yloxy)-3-azido-4-(tert-butyl-dimethyl siloxy)butan-2-ol (17) comprising;
i. reducing intermediate (17) obtained from the process of claim 1 in the presence of Pd/C in lower alcohol;
ii. protecting the amino group with isopropyl chloride in presence of a base and halogenated hydrocarbon as solvent;
iii. deprotecting the terminal alcohol group with Camphorsulfonic Acid (CSA) (2S,3S)-4-(2,3-dihydro-4-methyl-1H-inden-7-yloxy)-2-(isopropylamino)butane-1,3-diol) in lower alcohol at room temperature ranging between 25-35° C.;
iv. reacting the product of step (iii) with p-TsCl (p-Toluenesulfonyl chloride) in presence of a base and halogenated hydrocarbon as solvent at temperature ranging between 0° C. to 25° C.; and
v. reducing the compound of step (iv) with LiAlH$_4$ in THF at reflux to obtain antihypertensive agent ICI118.

In still another embodiment, lower alcohol used in step (i) and (iii) is selected from the group consisting of methanol or ethanol.

In still another embodiment, base used in step (ii) and (iv) is selected from the group consisting of ethylamine, triethylamine or pyridine.

In still another embodiment, halogenated solvent used in step (ii) and (iv) is selected from the group consisting of chloroform, carbon tetrachloride or Dichloromethane.

DESCRIPTION OF THE INVENTION

The invention will now be described in detail in connection with certain preferred and optional embodiments, so that various aspects thereof may be more fully understood and appreciated.

The present invention relates to efficient catalytic route to obtain enantiomerically pure α-aryloxy-α'-Azido/Alkoxy alcohols, which are valuable building blocks for bioactive pharmaceuticals, from anti and syn azido/alkoxy racemic epoxides.

The present invention relates to a single step process for the synthesis of α-Aryloxy-α'-Azido/Alkoxy alcohols of formula A with two stereocenters by phenolic kinetic resolution,

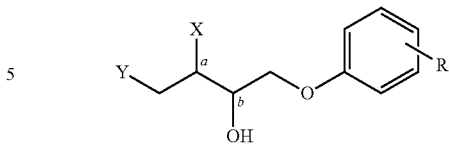

Formula A

Wherein X is selected from N$_3$ and OBn;
'R' is selected independently from hydrogen, alkyl (C$_1$-C$_5$), alkenyls (C$_2$-C$_6$), alkynyls (C$_2$-C$_6$), aryl, alkoxy, cyano, halo, nitro, —C(O)—R$_1$, —CO$_2$R$_2$, hydroxyl, —NH(R$_3$), cycloalkyl, cycloalkenyl, thiols, thiocarbonyl, sulfonyl or a heterocycle(C$_3$-C$_5$), where R$_1$, R$_2$ and R$_3$ represent hydrogen, alkyl(C$_1$-C$_5$).
Y denotes TBSO or phenyl; and
'a' and 'b' denote syn or anti position
Wherein the said process consists of comprising;
adding racemic epoxide of formula 1,

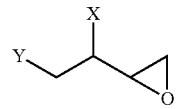

Formula 1 to phenol of formula 2

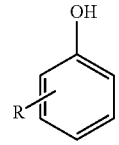

wherein, X, Y, and R are as defined above,
at room temperature to preformed (salen) Co (III) catalyst (formula 3),

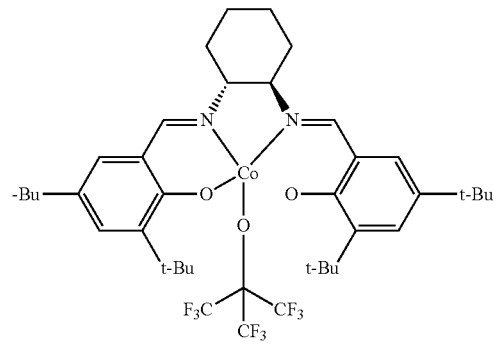

Formula 3

(R,R)-Co salen complex 3 followed by addition of tertiary butyl methyl ether, stirring and adding pyridinium p-toluene sulfonate, filtering, concentrating, followed by purifying to obtain the desired enantiopure product.

The catalyst for the reaction is prepared by oxidizing commercially available Co (II) salen complex with (CF$_3$)$_3$COH in the solvent for 45-50 min, stirring followed by removing the solvent by rotary evaporation to obtain Co (III) salen catalyst (formula 3).

In an aspect, the present invention provides phenolytic kinetic resolution of anti-azido/alkoxy epoxides. The process is schematically given below:

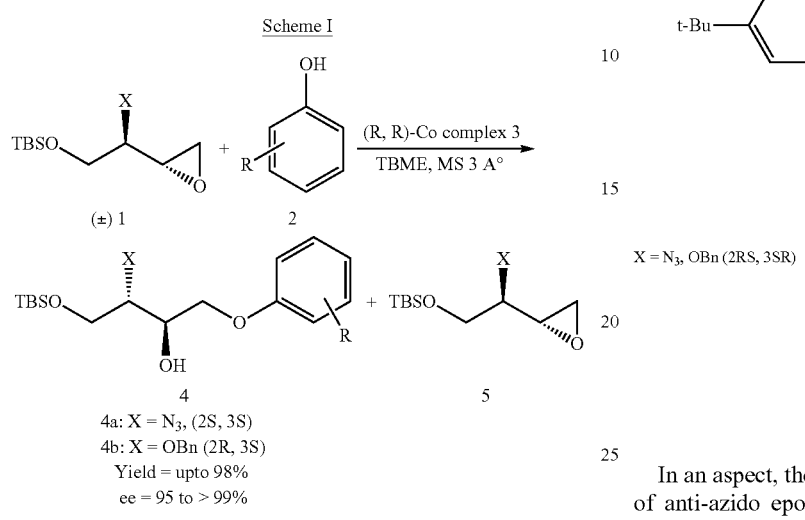

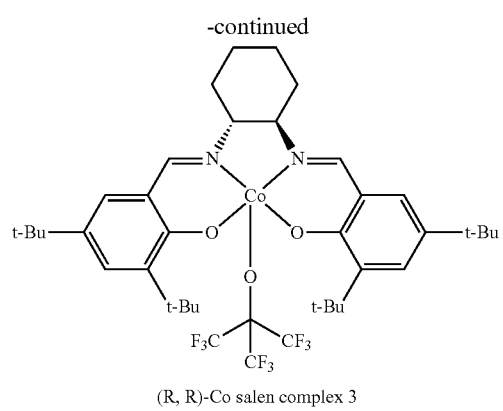

(R, R)-Co salen complex 3

X = N₃, OBn (2RS, 3SR)

In an aspect, the products of phenolytic kinetic resolution of anti-azido epoxides of the current invention are given below in Table 1:

TABLE 1

| | Phenolytic kinetic resolution of anti-azido epoxides of the present invention | | | |
|---|---|---|---|---|
| Sr. No. | Substrate Scope 2 | Product 4 | % Yield[a] of 4 | ee (%)[b] |
| 1 | phenol (OH) | (2S,3S)-3-azido-4-(tert-butyl-dimethyl siloxy)-1-phenoxybutan-2-ol | 65 | 95 |
| 2 | p-cresol (OH) | (2S,3S)-1-(p-tolyloxy)-3-azido-4-(tert-butyl-dimethyl siloxy)butan-2-ol | 72 | 97 |
| 3 | m-cresol (OH) | (2S,3S)-1-(m-tolyloxy)-3-azido-4-(tert-butyl-dimethylsiloxy)butan-2-ol | 70 | 98 |

TABLE 1-continued

Phenolytic kinetic resolution of anti-azido epoxides of the present invention

| Sr. No. | Substrate Scope 2 | Product 4 | % Yield[a] of 4 | ee (%)[b] |
|---|---|---|---|---|
| 4 | 2-methylphenol | (2S,3S)-1-(o-tolyloxy)-3-azido-4-(tert-butyl-dimethyl siloxy)butan-2-ol | 35 | 96 |
| 5 | 4-tert-butylphenol | (2S,3S)-1-(4-tert-butylphenoxy)-3-azido-4-(tert-butyl-dimethylsiloxy)butan-2-ol | 76 | 99 |
| 6 | 3-methoxyphenol | (2S,3S)-1-(3-methoxyphenoxy)-3-azido-4-(tert-butyl-dimethylsiloxy)butan-2-ol | 60 | 98 |
| 7 | 4-cyanophenol | 4-((2S,3S)-(3-azido-4-(tert-butyl-dimethyl siloxy)-2-hydroxybutoxy)benzonitrile | 87 | 96 |
| 8 | 4-nitrophenol | (2S,3S)-1-(4-nitrophenoxy)-3-azido-4-(tert-butyl-dimethyl siloxy)butan-2-ol | 84 | 98 |
| 9 | 4-fluorophenol | (2S,3S)-1-(4-fluorophenoxy)-3-azido-4-(tert-butyl-dimethyl siloxy)butan-2-ol | 72 | 99 |

TABLE 1-continued

Phenolytic kinetic resolution of anti-azido epoxides of the present invention

| Sr. No. | Substrate Scope 2 | Product 4 | % Yield[a] of 4 | ee (%)[b] |
|---|---|---|---|---|
| 10 | 4-bromophenol | (2S,3S)-1-(4-bromophenoxy)-3-azido-4-(tert-butyl-dimethyl siloxy) butan-2-ol | 86 | 97 |
| 11 | 4-chlorophenol | (2S,3S)-1-(4-chlorophenoxy)-3-azido-4-(tert-butyl-dimethyl siloxy)butan-2-ol | 90 | 96 |
| 12 | 3,5-dichlorophenol | (2S,3S)-1-(3,5-diehlorophenoxy)-3-azido-4-tert-butyl-dimethyl siloxy)butan-2-ol | 89 | 95 |
| 13 | 4'-hydroxyacetophenone | 1-(4-(2S,3S)-(3-azido-4-(tert-butyl-dimethyl siloxy)-2-hydroxybutoxy)phenyl)ethanone | 88 | 99 |
| 14 | 4-hydroxybenzaldehyde | 4-((2S,3S)-(3-azido-4-tert-butyl-dimethyl siloxy)-2-hydroxybutoxy)benzaldehyde | 95 | 96 |
| 15 | 5-bromosalicylaldehyde | 2-(2S,3S)-(3-azido-4-(tert-butyl-dimethyl siloxy)-2-hydroxybutoxy)-5-bromobenzaldehyde | 58 | 97 |

TABLE 1-continued

Phenolytic kinetic resolution of anti-azido epoxides of the present invention

| Sr. No. | Substrate Scope 2 | Product 4 | % Yield[a] of 4 | ee (%)[b] |
|---|---|---|---|---|
| 16 | 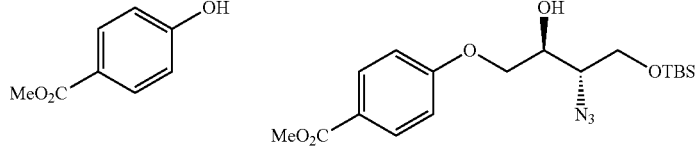 | 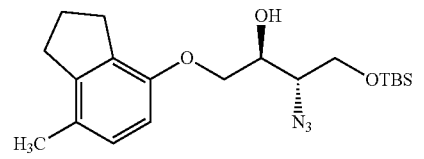  methyl 4-((2S,3S)-(3-azido-4-(tert-butyl-dimethyl siloxy)-2-hydroxybutoxy)benzoate | 96 | 95 |
| 17 | 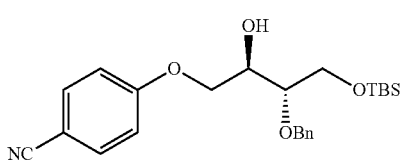 | 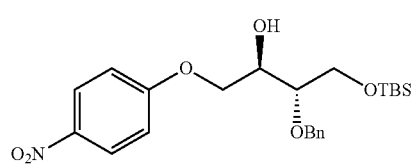  (2S,3S)-1-(2,3-dihydro-4-methyl-1H-inden-7-yloxy)-3-azido-4-(tert-butyl-dimethyl siloxy)butan-2-ol | 75 | 99 |

[a] Isolated yield after column chromatographic purification with respect to phenol (2).
[b] ee enantiomeric excess determined by chiral HPLC analysis.

In yet another aspect, the products of phenolytic kinetic resolution of anti-alkoxy epoxides of the current invention are given below in Table 2:

TABLE 2

Phenolytic kinetic resolution of anti-alkoxy epoxides of present invention

| Sr. No. | Substrate Scope 2 | Product 4 | % Yield[a] of 4 | ee (%)[b] |
|---|---|---|---|---|
| 1 | (image) | (image)  4-((2R,3S)-4-(tert-butyl dimethylsiloxy)-3-(benzyloxy)-2-hydroxybutoxy)benzonitrile | 87 | 98 |
| 2 | (image) | (image)  (2R,3S)-4-(tert-butyl dimethylsiloxy)-1-(4-nitrophenoxy)-3-(benzyloxy)butan-2-ol | 89 | 96 |

TABLE 2-continued

Phenolytic kinetic resolution of anti-alkoxy epoxides of present invention

| Sr. No. | Substrate Scope 2 | Product 4 | % Yield[a] of 4 | ee (%)[b] |
|---|---|---|---|---|
| 3 | (4-hydroxyphenyl methyl ketone) | 1-(4-((2R,3S)-4-(tert-butyl dimethylsiloxy)-3-(benzyloxy)-2-hydroxybutoxy)phenyl)ethanone | 98 | 98 |
| 4 | (4-hydroxybenzaldehyde) | 4-((2R,3S)-4-(tert-butyl dimethylsiloxy)-3-(benzyloxy)-2-hydroxybutoxy)benzaldehyde | 75 | 99 |
| 5 | (methyl 4-hydroxybenzoate) | methyl 4-((2R,3S)-4-(tert-butyl dimethylsiloxy)-3-(benzyloxy)-2-hydroxybutoxy)benzoate | 81 | 97 |
| 6 | (2,4,5-trichlorophenol) | (2R,3S)-1-(2,4,5-trichlorophenoxy)-4-(tert-butyl dimethylsiloxy)-3-(benzyloxy)butan-2-ol | 87 | 98 |

[a]Isolated yield after column chromatographic purification with respect to phenol (2).
[b]ee enantiomeric excess determined by chiral HPLC analysis.

In another aspect, the present invention provides a phenolytic kinetic resolution of syn-azido/alkoxy epoxides which is schematically given below:

Scheme 2:

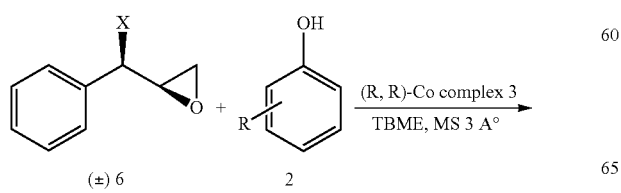
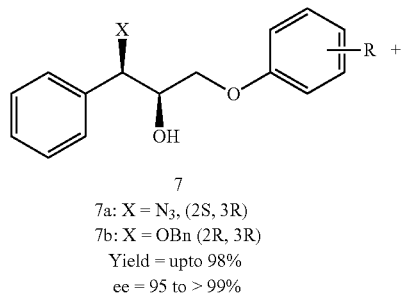

7
7a: X = N$_3$, (2S, 3R)
7b: X = OBn (2R, 3R)
Yield = upto 98%
ee = 95 to > 99%

-continued

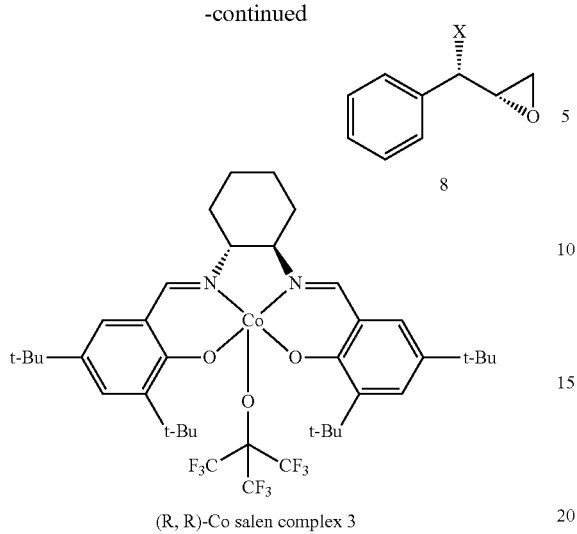

(R, R)-Co salen complex 3

X = N₃, OBn (2RS, 3SR)

In another aspect, the products of phenolytic kinetic resolution of syn-azido epoxides of the current invention are given below in Table 3:

TABLE 3

Phenolytic kinetic resolution of syn-azido epoxides of present invention

| Sr. No. | Substrate 2 | Product 7 | % Yield[a] of 7 | ee (%)[b] |
|---|---|---|---|---|
| 1 | (4-hydroxyphenyl methyl ketone) | 1-(4-((2S,3R)-3-azido-2-hydroxy-3-phenylpropoxy)phenyl)ethanone | 93 | 98 |
| 2 | (methyl 4-hydroxybenzoate) | methyl 4-((2S,3R)-3-azido-2-hydroxy-3-phenylpropoxy)benzoate | 95 | 99 |
| 3 | (4-nitrophenol) | (1R,2S)-3-(4-nitrophenoxy)-1-azido-1-phenylpropan-2-ol | 96 | 96 |

[a] Isolated yield after column chromatographic purification with respect to phenol (2).
[b] ee enantiomeric excess determined by chiral HPLC analysis.

In yet another aspect, the products of phenolytic kinetic resolution of syn-alkoxy epoxides of the current invention are given below in Table 4:

TABLE 4

Phenolytic kinetic resolution of syn-alkoxy epoxides of present invention

| Sr. No. | Substrate 2 | Product 7 | % Yield[a] of 7 | ee (%)[b] |
|---|---|---|---|---|
| 1 | ![substrate] | ![product] 1-(4-((2R,3R)-3-(benzyloxy)-2-hydroxy-3-phenylpropoxy)phenyl)ethanone | 89 | 97 |

[a]Isolated yield after column chromatographic purification with respect to phenol (2).
[b]ee enantiomeric excess determined by chiral HPLC analysis.

In another aspect, the present invention provides asymmetric synthesis of antihypertensive agent ICI118,551 from compound of formula (17) as given below:

Scheme 3:

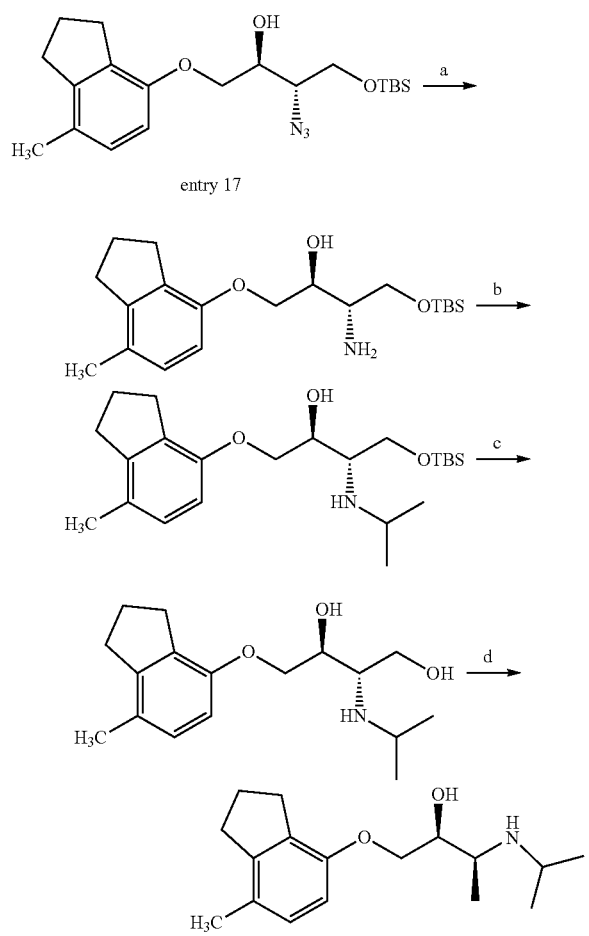

Reaction Condition: a) $H_2$/Pd—C, MeOH; b) $Et_3N$, $^iPrCl$, $CH_2Cl_2$; c) CSA, MeOH, rt.; d) i) p-TsCl, $Et_3N$, $CH_2Cl_2$, 0° C.; ii) $LiAlH_4$, THF, reflux.

The Asymmetric synthesis of antihypertensive agent ICI118,551 ((2S,3S)-1-(2,3-dihydro-4-methyl-1H-inden-7-yloxy)-3-(isopropylamino)butan-2-ol) from intermediate (17) comprises;
i. Reducing intermediate (17) obtained from the process of claim 1 in presence of Pd/C in lower alcohol;
ii. Protecting the amino group with isopropyl chloride in presence of a base and halogenated hydrocarbon as solvent;
iii. Deprotecting the terminal alcohol group with CSA in lower alcohol at room temperature; and
iv. Reacting the product of step (iii) with p-TsCl in presence of a base and halogenated hydrocarbon as solvent at 0° C.; and
v. Reducing the compound of step (iv) with $LiAlH_4$ in THF at reflux to obtain the desired product.

The base is selected from methylamine, ethylamine, triethylamine, pyridine etc. The halogenated hydrocarbons are selected from chloroform, carbon tetrachloride, etc. The lower alcohols are selected from $C_1$-$C_6$ alcohols.

The phenolytic kinetic resolution provides atom economic synthesis of α-Aryloxy-α'-Azido/Alkoxy alcohols of high optical purity in high yield.

INDUSTRIAL ADVANTAGES

The applicant sates that the kinetic resolution technique published in Chem Comm. (disclosed above in the article) limits itself to the use of only water as the nucleophile for the production of two-chiral centered resolution products (syn\anti azido/alkoxy diols and epoxides). In the present work, however, any phenol can be employed as nucleophile, for the first time, in the two-chiral centered resolution process for effective Phenolytic Kinetic Resolution of syn/anti azido/alkoxy epoxides, which indeed resulted in products (syn/anti α-Aryloxy α'-azido/alkoxy alcohols) with high enantiomeric excess and yields.

The products (syn/anti α-Aryloxy-α'-azido/alkoxy alcohols) obtained in the present work after Phenolytic Kinetic Resolution are entirely different from products obtained in the publication in Chem Comm (syn\anti azido/alkoxy diols and epoxides).

With the present method, less number of steps (atom economy) is involved to make certain bioactive compounds; otherwise it requires multi-steps leading to low yields and % ee of the final products.

Selective protection of diols is generally tedious but the present method provides a simple procedure to produce mono-protected diols as aryl ethers.

Bioactive molecules which are difficult to synthesize using previous method can now be synthesized easily using present method for e.g. ICI-118,551.

The yields obtained in present method are excellent up to 99% based on phenol as compared to 48% reported in the Chem Comm paper.

The following examples are given by way of illustration and therefore should not be construed to limit the scope of the present invention

EXAMPLE

General Experimental Procedure for Phenolytic Kinetic Resolution

Preparation of Catalyst

Commercially available (salen) Co(II) complex (0.302 g, 0.500 mmol) was effectively oxidized to (salen) Co(III) complex (3) simply by stirring it with $(CF_3)_3COH$ (1.180 g, 5.00 mmol) in $CH_2Cl_2$ (5.0 mL) open to the atmosphere for 45 min and then removing the solvent by rotary evaporation.

General Procedure for the Phenolytic Kinetic Resolutions of Syn and Anti Azido/Alkoxy Epoxide (Scheme 1 and 2)

A 10 mL flask was charged with 86 mg (0.100 mmol) of catalyst (3) and 100 mg MS 3 Å. Epoxide (5.00 mmol) (1) or (6) and phenol (2.25 mmol) (2) were added at room temperature, followed by addition of TBME (0.15 mL). The reaction was stirred at room temperature until complete conversion of phenol, at which time 75 mg (0.30 mmol) pyridinium p-toluenesulfonate was added. The reaction mixture was filtered through a pad of silica and washed with 50% EtOAc/hexanes. The filtrate was concentrated and purified by chromatography on silica gel with EtOAc/hexanes. The enantiomeric purity was determined by GC or HPLC.

Spectral Studies of the Products

1. Compound of (2S,3S)-3-azido-4-(tert-butyl-dimethyl siloxy)-1-phenoxybutan-2-ol 1 (Table 1)

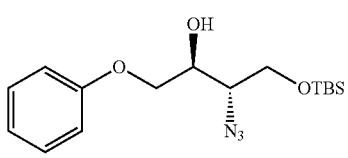 [SMILES: CC(C)(C)[Si](C)(C)OC[C@H](N=[N+]=[N-])[C@H](O)COc1ccccc1]

Yield: 65%; gum; IR (CHCl$_3$, cm$^{-1}$): 690, 752, 837, 1042, 1108, 1243, 1497, 1599, 2099, 2857, 2929, 2953, 3460; $^1$H NMR (200 MHz, CDCl$_3$) δ 012 (s, 6H), 0.93 (s, 9H), 2.67 (d, J=5.02 Hz, 1H), 4.03 (m, 5H), 6.93 (m, 3H), 7.31 (m, 2H) 2H); $^{13}$C NMR (50 MHz, CDCl$_3$): −5.59, 18.18, 25.78, 63.44, 63.74, 69.59, 68.99, 114.54, 121.35, 129.51, 158.21; Anal. Calcd. for C$_{16}$H$_{27}$N$_3$O$_3$Si requires C, 56.94; H, 8.06; N, 12.45%. found C, 56.92; H, 8.04; N, 12.43%.

2. Compound of (2S,3S)-1-(p-tolyloxy)-3-azido-4-(tert-butyl-dimethyl siloxy)butan-2-ol 2 (Table 1)

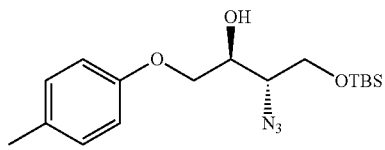 [SMILES: Cc1ccc(OC[C@@H](O)[C@H](CO[Si](C)(C)C(C)(C)C)N=[N+]=[N-])cc1]

Yield: 72%; gum; IR (CHCl$_3$, cm$^{-1}$): 777, 838, 1047, 1109, 1172, 1258, 1289, 1462, 1490, 1586, 1603, 2098, 2857, 2284, 2929, 2953, 3451; $^1$H NMR (200 MHz, CDCl$_3$) δ 0.12 (s, 6H), 0.92 (s, 9H), 2.29 (s, 1H), 2.67 (d, J=4.987 Hz, 1H) 3.56 (m, 1H), 4.00 (dm, 5H), 6.8. (d, J=8.58 Hz, 2H), 7.06 (d, J=8.49 Hz, 2H); $^{13}$C NMR (50 MHz, CDCl$_3$): 21-5.53, 18.25, 20.52, 25.84, 63.55, 63.82, 69.82, 69.24, 69.65, 11.49, 130, 130.56, 156.20; Anal. Calcd. for C$_{17}$H$_{29}$N$_3$O$_3$Si requires C, 57.92; H, 8.58; N, 11.92%. found C, 57.90; H, 8.56; N, 11.90%.

3. Compound of 4-((2S,3S)-(3-azido-4-(tert-butyl-dimethyl siloxy)-2-hydroxybutoxy)benzonitrile 7 (table 1)

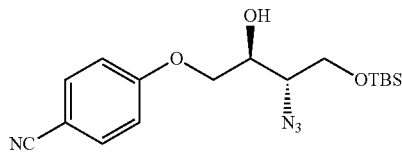 [SMILES: CC(C)(C)[Si](C)(C)OC[C@H](N=[N+]=[N-])[C@H](O)COc1ccc(C#N)cc1]

Yield: 87%; gum; IR (CHCl$_3$, cm$^{-1}$): 778, 836, 1031, 1111, 1172, 1257, 1463, 1471, 1509, 1609, 2099, 2226, 2857 2929, 2953, 2445; $^1$H NMR (200 MHz, CDCl$_3$) δ 0.012 (s, 6H), 0.92 (s, 9H), 2.70 (d, J=4.93 Hz, 1H 1H), 3.50 (m, 1H), 4.03 (m, 1H), 4.03 (m, 5H), 6.98 (d, J=9.13 Hz, 2H), 7.59 (d, J=8.77 Hz, 2H); $^{13}$C NMR (50 MHz, CDCl3): −5.58, 18.18, 25.77, 63.14, 63.62, 69.55, 69.62, 115.30, 133.98, 161.80; Anal. Calcd. for C$_{17}$H$_{26}$N$_4$O$_3$Si requires C, 56.17; H, 7.49; N, 15.41%. found C, 56.15; H, 7.47; N, 15.39%.

4. Compound of (2S,3S)-1-(4-chlorophenoxy)-3-azido-4-(tert-butyl-dimethylsiloxy)butan-2-ol 11 (Table 1)

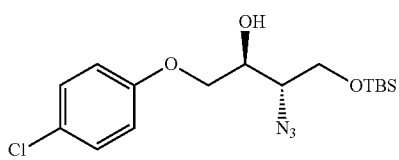 [SMILES: CC(C)(C)[Si](C)(C)OC[C@H](N=[N+]=[N-])[C@H](O)COc1ccc(Cl)cc1]

Yield: 90 gum; IR (CHCl$_3$, cm$^{-1}$): 778, 837, 1095, 1243, 1492, 2100, 2858, 2929, 2953, 3446; $^1$H NMR (200 MHz, CDCl3) δ 0.12 (s, 6H), 0.93 (s, 9H), 2.66 (d, J=4.67, 1H), 3.59 (m, 1H), 4.02 (m, 5H), 6.85 (d, J=8.95 Hz, 2H), 7.44 (d, J=8.86 Hz, 2H); $^{13}$C NMR (50 MHz, CDCl$_3$): −5.59, 18.18, 25.77, 63.70, 63.25, 69.47, 69.62, 115.81, 126.35, 129.40, 156.83; Anal. Calcd. for $C_{16}H_{26}ClN_3O_3Si$ requires C, 51.53; H, 7.30; N, 11.27%. found C, 51.50; H, 7.28; N, 11.25%.

5. Compound of methyl 4-((2S,3S)-(3-azido-4-(tert-butyl-dimethylsiloxy)-2-hydroxybutoxy)benzoate 16 (Table 1)

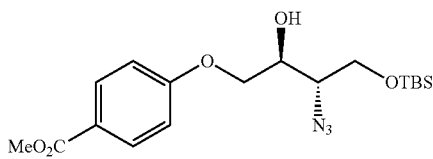 [SMILES: COC(=O)c1ccc(OC[C@@H](O)[C@H](CO[Si](C)(C)C(C)(C)C)N=[N+]=[N-])cc1]

Yield: 81%; gum; IR (CHCl$_3$, cm$^{-1}$): 771, 839, 1112, 1170, 1254, 1283, 1436, 1511, 1606, 1716, 2099, 2857, 2930, 3471; $^1$H NMR (200 MHz, CDCl$_3$) δ 0.13 (s, 6H), 0.93 (s, 9H), 2.73 (d, J=5.05 Hz, 1H), 3.61 (m, 1H), 3.89 (s, 1H), 4.01 (m, 3H), 4.17 (m, 2H), 6.94 (d, J=9.00 Hz, 2H), 7.88 (d, J=9.00 Hz, 2H); $^{13}$C NMR (50 MHz, CDCl$_3$): −5.57, 18.20, 25.79, 51.88, 63.28, 63.71, 69.34, 69.69 114.13, 123.19, 131.67, 162, 166.61; Anal. Calcd. for $C_{18}H_{29}N_3O_5Si$ requires C, 54.52; H, 7.63; N, 10.60%. found C, 54.50; H, 7.61; N, 10.58%.

6. Compound of (2S,3S)-1-(3-methoxyphenoxy)-3-azido-4-(tert-butyl-dimethylsiloxy)butan-2-ol 6 (Table 1)

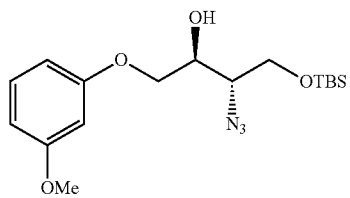 [SMILES: COc1cccc(OC[C@@H](O)[C@H](CO[Si](C)(C)C(C)(C)C)N=[N+]=[N-])c1]

Yield: 60%; gum; IR (CHCl$_3$, cm$^{-1}$): 771, 839, 1112, 1170, 1254, 1283, 1436, 1511, 1606, 1716, 2099, 2857, 2930, 3471; $^1$H NMR (200 MHz, CDCl$_3$) δ 0.12 (s, 6H), 0.93 (s, 9H), 2.67-2.68 (dd, J=3.05 Hz, 1H), 3.97 (m, 1H), 3.78 (s, 1H), 4.2-4.06 (m, 3H), 4.09-4.17 (dd, J=3.36, 9.50, 1H), 6.46-6.51 (m, 2H), 7.19 (t, 1H); $^{13}$C NMR (50 MHz, CDCl$_3$): −5.23, 18.55, 26.15, 55.48, 63.79, 64.09, 70.00, 101.54, 107.05, 107.36, 130.327, 159.84, 161.24; Anal. Calcd. for $C_{17}H_{29}N_3O_4Si$ requires C, 55.56; H, 7.95; N, 11.43%. found C, 55.25; H, 7.85; N, 11.35%.

7. Compound of (2S,3S)-1-(3,5-dichlorophenoxy)-3-azido-4-tert-butyldimethyl)butan-2-ol 12 (Table 1)

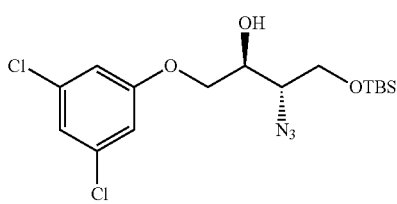 [SMILES: CC(C)(C)[Si](C)(C)OC[C@H](N=[N+]=[N-])[C@H](O)COc1cc(Cl)cc(Cl)c1]

Yield: 89%; gum; IR (CHCl$_3$, cm$^{-1}$): 771, 839, 1112, 1170, 1254, 1283, 1436, 1511, 1606, 1716, 2099, 2857, 2930, 3471; $^1$H NMR (200 MHz, CDCl$_3$) δ 0.12 (s, 6H), 0.92 (s, 9H), 2.73-2.75 (d, J=5.56 Hz, 1H), 3.57-3.66 (m, 1H), 3.88-4.20 (m, 5H), 6.85-6.90 (d, J=8.82 Hz, 1H), 7.16-7.21 (dd, J=2.53, 8.80 Hz, 1H), 7.36-7.37 (d, J=2.53, 1H); $^{13}$C NMR (50 MHz, CDCl$_3$): −5.50, 18.26, 25.85, 51.88, 63.39, 63.82, 69.43, 70.81, 114.65, 124.06, 126.75, 130.11, 152.68; Anal. Calcd. for $C_{16}H_{25}Cl_2N_3O_3Si$ requires C, 47.29; H, 6.20; N, 10.34%. found C, 47.18; H, 6.09; N, 10.40%.

8. Compound of 2-(2S,3S)-(3-azido-4-(tert-butyl-dimethylsiloxy)-2-hydroxybutoxy)-5-bromobenzaldehyde 15 (Table 1)

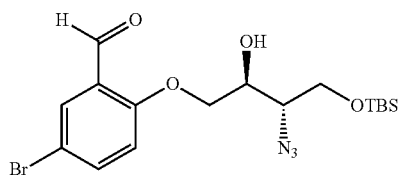 [SMILES: CC(C)(C)[Si](C)(C)OC[C@H](N=[N+]=[N-])[C@H](O)COc1ccc(Br)cc1C=O]

Yield: 58%; gum; IR (CHCl$_3$, cm$^{-1}$): 771, 839, 1112, 1170, 1254, 1283, 1436, 1511, 1606, 1716, 2099, 2857, 2930, 3471; $^1$H NMR (200 MHz, CDCl3) δ 0.13 (s, 6H), 0.92 (s, 9H), 3.56-3.64 (m, 1H), 3.90-4.10 (m, 3H), 4.16-4.29 (m, 2H), 6.90 (d, J=8.81 Hz, 1H), 7.60-7.66 (dd, J=2.61, 8.87 Hz, 1H), 7.87-7.88 (d, J=2.50, 1H), 10.28 (s, 1H); $^{13}$C NMR (50 MHz, CDCl$_3$): −6.18, 17.58, 25.16, 62.67, 63.06, 68.87, 70.00, 113.45, 114.46, 125.69, 131.78, 137.75, 158.76, 187.68; Anal. Calcd. for $C_{17}H_{26}BrN_3O_4Si$ requires C, 45.95; H, 5.90; N, 9.46%. found C, 45.90; H, 5.95; N, 9.48%.

9. Compound of 1-(4-(2S,3S)-(3-azido-4-(tert-butyl-dimethylsiloxy)-2-hydroxybutoxy)phenyl)ethanone 13 (Table 1)

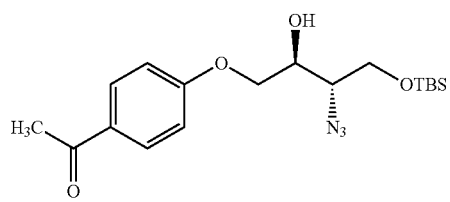 [SMILES: CC(=O)c1ccc(OC[C@@H](O)[C@H](CO[Si](C)(C)C(C)(C)C)N=[N+]=[N-])cc1]

Yield: 88%; gum; IR (CHCl$_3$, cm$^{-1}$): 777, 836, 1033, 1114, 1173, 1256, 1307, 1600, 2098, 2857, 2929, 2953, 3440; $^1$H NMR (200 MHz, CDCl$_3$) δ 0.13 (s, 6H), 0.93 (s, 9H), 2.56 (s, 3H), 2.73-2.76 (d, J=4.97 Hz, 1H), 3.55-3.67 (m, 1H), 3.89 4.24 (m, 5H), 6.93-6.98 (d, J=8.89 Hz, 2H), 7.91-7.95 (d, J=8.94 Hz, 2H); $^{13}$C NMR (50 MHz, CDCl$_3$): −5.58, 18.18, 25.78, 26.20, 63.40, 63.66, 69.47, 114.22, 130.62, 130.85, 162.27, 196.64; Anal. Calcd. for $C_{18}H_{29}N_3O_4Si$ requires C, 56.96; H, 7.70; N, 11.07%. found C, 56.92; H, 7.65; N, 11.02%.

10. Compound of (2S,3S)-1-(4-bromophenoxy)-3-azido-4-(tert-butyl-dimethylsiloxy)butan-2-ol 10 (Table 1)

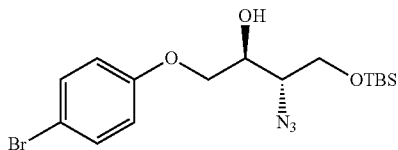

Yield: 86%; gum; IR (CHCl$_3$, cm$^{-1}$): 778, 837, 1003, 1072, 1103, 1242, 1488, 2099, 2857, 2929, 2953, 3461; $^1$H NMR (200 MHz, CDCl$_3$) δ 0.12 (s, 6H), 0.93 (s, 9H), 2.67-2.69 (d, J=4.73 Hz, 1H), 3.53-3.61 (m, 1H), 3.87-4.12 (m, 5H), 6.78-6.82 (m, 2H), 7.36-7.40 (m, 2H); $^{13}$C NMR (50 MHz, CDCl$_3$): −5.573, 18.22, 25.82, 63.28, 63.714, 69.66, 113.67, 116.36, 132.40, 157.39; Anal. Calcd. for C$_{16}$H$_{26}$BrN$_3$O$_3$Si requires C, 46.15; H, 6.29; N, 10.09%. found C, 46.10; H, 6.28; N, 10.05%.

11. Compound of (2S,3S)-1-(4-nitrophenoxy)-3-azido-4-(tert-butyl-dimethyl siloxy)butan-2-ol 8 (Table 1)

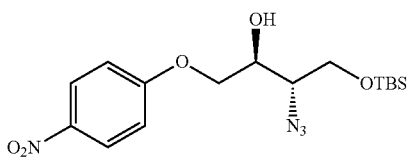 [SMILES: CC(C)(C)[Si](C)(C)OC[C@H](N=[N+]=[N-])[C@H](O)COc1ccc([N+](=O)[O-])cc1]

Yield: 87%; gum; IR (CHCl$_3$, cm$^{-1}$): 779, 840, 862, 1111, 1260, 1298, 1343, 1498, 1514, 1593, 1608, 2100, 2857, 2929, 2954, 3461; $^1$H NMR (200 MHz, CDCl$_3$) δ 0.13 (s, 6H), 0.93 (s, 9H), 2.72-2.75 (d, J=4.86 Hz, 1H), 3.56-3.65 (m, 1H), 3.91-4.07 (m, 3H), 4.13-4.28 (m, 2H), 6.98-7.03 (d, J=9.35 Hz, 2H), 8.20-8.24 (d, J=9.31 Hz, 2H); $^{13}$C NMR (50 MHz, CDCl$_3$): −5.56, 18.21, 25.79, 63.14, 63.66, 69.67, 70.09, 114.59, 125.92, 141.89, 163.35; Anal. Calcd. for C$_{16}$H$_{26}$N$_4$O$_5$Si requires C, 50.24; H, 6.85; N, 14.65%. found C, 50.22; H, 6.87; N, 14.68%.

12. Compound of (2S,3S)-1-(4-fluorophenoxy)-3-azido-4-(tert-butyldimethylsiloxy)butan-2-ol 9 (Table 1)

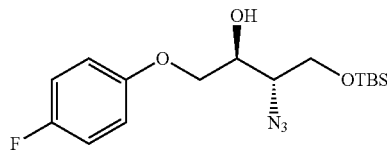 [SMILES: CC(C)(C)[Si](C)(C)OC[C@H](N=[N+]=[N-])[C@H](O)COc1ccc(F)cc1]

Yield: 72%; gum; IR (CHCl$_3$, cm$^{-1}$): 778, 836, 1098, 1220, 1252, 1507, 2100, 2858, 2930, 2953, 3440; $^1$H NMR (200 MHz, CDCl$_3$) δ 0.12 (s, 6H), 0.93 (s, 9H), 2.67-2.70 (d, J 5.08 Hz, 1H), 3.53-3.62 (m, 1H), 3.87-4.11 (m, 5H), 6.82-6.89 (m, 2H), 6.94-6.98 (m, 2H); $^{13}$C NMR (50 MHz, CDCl3): −5.54, 18.24, 25.82, 63.39, 63.77, 69.69, 115.58, 115.74, 116.20, 154.39, 155.23; Anal. Calcd. for C$_{16}$H$_{26}$FN$_3$O$_3$Si requires C, 54.06; H, 7.37; N, 11.82%. found C, 54.08; H, 7.35; N, 11.81%.

13. Compound of (2S,3S)-1-(m-tolyloxy)-3-azido-4-(tert-butyl-dimethylsiloxy)butan-2-ol 3 (Table 1)

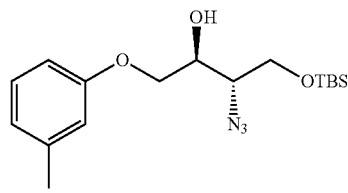 [SMILES: Cc1cccc(OC[C@@H](O)[C@H](CO[Si](C)(C)C(C)(C)C)N=[N+]=[N-])c1]

Yield: 70%; gum; IR (CHCl$_3$, cm$^{-1}$): 774, 838, 1109, 1172, 1258, 1289, 1462, 1500, 1603, 2098, 2857, 2884, 2929, 2953, 3451; NMR (200 MHz, CDCl$_3$) δ 0.12 (s, 6H), 0.93 (s, 9H), 2.33 (s, 3H), 2.65-2.68 (d, J=4.84 Hz, 1H), 3.53-3.62 (m, 1H), 3.87-4.13 (m, 5H), 6.69-6.80 (m, 3H), 7.12-7.20 (m, 1H); $^{13}$C NMR (50 MHz, CDCl$_3$): −5.52, 18.25, 21.53, 25.85, 63.55, 63.80, 69.02, 69.63 111.56, 115.43, 122.25, 129.30, 139.51, 158.30; Anal. Calcd. for C$_{17}$H$_{29}$N$_3$O$_3$Si requires C, 58.09; H, 8.32; N, 11.95%. found C, 58.11; H, 8.35; N, 11.85%.

14. Compound of (2S,3S)-1-(o-tolyloxy)-3-azido-4-(tert-butyl-dimethylsiloxy)butan-2-ol 4 (Table 1)

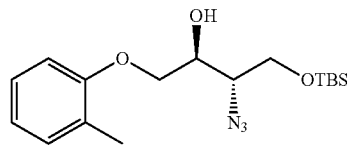 [SMILES: Cc1ccccc1OC[C@@H](O)[C@H](CO[Si](C)(C)C(C)(C)C)N=[N+]=[N-]]

Yield: 35%; gum; IR (CHCl$_3$, cm$^{-1}$): 774, 838, 1109, 1172, 1258, 1289, 1462, 1500, 1603, 2098, 2857, 2884, 2929, 2953, 3451; $^1$H NMR (200 MHz, CDCl$_3$) δ 0.12 (s, 6H), 0.93 (s, 9H), 2.24 (s, 3H), 2.63-2.65 (d, J=5.36 Hz, 1H), 3.57-3.65 (m, 1H), 3.88-3.95 (m, 3H), 4.02-4.13 (m, 2H), 6.81-6.91 (m, 2H), 7.11-7.15 (m, 2H); $^{13}$C NMR (50 MHz, CDCl$_3$): −5.58, 16.23, 18.19, 25.78, 29.67, 63.57, 63.82, 68.99, 69.75, 111.25, 121.11, 126.54, 126.90, 130.79, 156.52; Anal. Calcd. for C$_{17}$H$_{29}$N$_3$O$_3$Si requires C, 58.09; H, 8.32; N, 11.95%. found C, 58.02; H, 8.35; N, 11.98%.

15. Compound of (2S,3S)-1-(4-tert-butylphenoxy)-3-azido-4-(tert-butyldimethylsiloxy)butan-2-ol 5 (Table 1)

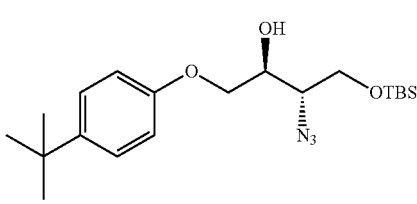 [SMILES: CC(C)(C)c1ccc(OC[C@@H](O)[C@H](CO[Si](C)(C)C(C)(C)C)N=[N+]=[N-])cc1]

Yield: 76%; gum; IR (CHCl$_3$, cm$^{-1}$): 777, 836, 1113, 1243, 1513, 2095, 2858, 2929, 2956, 3460; $^1$H NMR (200 MHz, CDCl$_3$) δ 0.12 (s, 6H), 0.92 (s, 9H), 1.30 (s, 9H), 2.65-2.68 (d, 5.24 Hz, 1H), 3.53-3.62 (m, 1H), 3.80-4.14 (m, 5H), 6.82-6.86 (m, 2H), 7.27-7.31 (m, 2H); $^{13}$C NMR (50 MHz, CDCl$_3$): −5.48, 18.28, 25.88, 31.60, 34.16, 63.50, 63.86, 69.12, 69.68, 114.15, 126.35, 144.10, 156.05; Anal. Calcd. for C$_{20}$H$_{35}$N$_3$O$_3$Si requires C, 61.03; H, 8.96; N, 10.68%. found C, 61.08; H, 8.92; N, 10.63%.

16. Compound of 4-((2S,3S)-(3-azido-4-tert-butyldimethylsiloxy)-2-hydroxybutoxy)benzaldehyde 14 (Table 1)

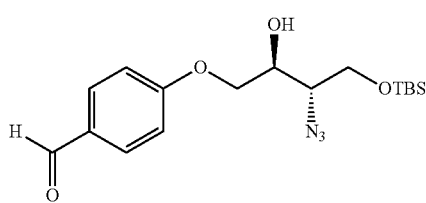 [SMILES: CC(C)(C)[Si](C)(C)OC[C@H](N=[N+]=[N-])[C@H](O)COc1ccc(C=O)cc1]

Yield: 95%; gum; IR (CHCl$_3$, cm$^{-1}$): 778, 836, 1110, 1167, 1258, 1509, 1578, 1601, 1689, 2099, 2857, 2884, 2929, 3440; $^1$H NMR (200 MHz, CDCl$_3$) δ 0.123 (s, 6H), 0.93 (s, 9H), 2.77-2.80 (d, J=5.06 Hz, 1H), 3.56-3.65 (m, 1H), 3.95-4.06 (m, 3H), 4.16-4.27 (m, 2H), 7.01-7.05 (m, 2H), 7.82-7.87 (m, 2H), 9.89 (s, 1H); $^{13}$C NMR (50 MHz, CDCl$_3$): −5.53, 18.22, 25.82, 63.31, 63.69, 69.61, 114.88, 130.39, 132.04, 163.34, 190.61; Anal. Calcd. for C$_{17}$H$_{27}$N$_3$O$_4$Si requires C, 55.86; H, 7.45; N, 11.50%. found C, 55.90; H, 7.46; N, 11.53%.

17. Compound of (1R,2S)-3-(4-nitrophenoxy)-1-azido-1-phenylpropan-2-ol 3 (table 3):

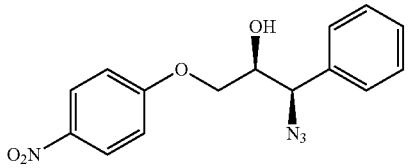 [SMILES: [N-]=[N+]=N[C@H](c1ccccc1)[C@H](O)COc1ccc([N+](=O)[O-])cc1]

Yield: 90%; gum; IR (CHCl$_3$, cm$^{-1}$): 702, 752, 845, 1111, 1167, 1260, 1342, 1510, 1592, 2105, 3481; $^1$H NMR (200 MHz, CDCl3) δ 2.63-2.65 (d, 0.1=4.26, 1H), 3.80-3.87 (dd, 4.83, 9.80 Hz, 1H), 4.00-4.17 (m, 2H), 4.78-4.82 (d, J=7.30 Hz, 1H), 6.88-6.92 (m, 2H), 7.35-7.41 (m, 5H), 8.16-8.20 (m, 2H); $^{13}$C NMR (50 MHz, CDCl$_3$): 67.83, 68.83, 73.18, 114.47, 125.83, 132.04, 127.47, 129.12, 135.80, 141.88, 163.15; Anal. Calcd. for C$_{15}$H$_{14}$N$_4$O$_4$ requires C, 57.32; H, 4.49; N, 17.83%. found C, 57.28; H, 4.44; N, 17.82%.

18. Compound of 1-(4-((2S,3R)-3-azido-2-hydroxy-3-phenylpropoxy)phenyl)ethanone 1 (table 3)

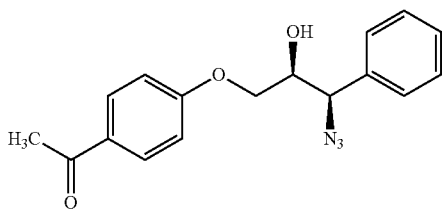 [SMILES: CC(=O)c1ccc(OC[C@@H](O)[C@H](N=[N+]=[N-])c2ccccc2)cc1]

Yield: 88%; gum; IR (CHCl$_3$, cm$^{-1}$): 775, 845, 1110, 1173, 1254, 1359, 1599, 1671, 2104, 3426; $^1$H NMR (200 MHz, CDCl$_3$) δ 2.54 (s, 3H), 2.65-2.67 (d, J=4.63, 1H), 3.77-3.84 (dd, J=4.80, 9.7 Hz, 1H), 3.96-4.13 (m, 2H), 4.79-4.82 (d, J=7.38 Hz, 1H), 6.84-6.88 (m, 2H), 7.32-7.41 (m, 5H), 7.87-7.92 (m, 2H); $^{13}$C NMR (50 MHz, CDCl$_3$): 26.25, 67.81, 68.42, 73.30, 114.17, 127.52, 128.89, 129.00, 130.59, 136.14, 162.16, 196.73; Anal. Calcd. for C$_{17}$H$_{17}$N$_3$O$_3$ requires C, 65.58; H, 5.50; N, 13.50%. found C, 65.54; H, 5.48; N, 13.48%.

19. Compound of 1-(4-((2R,3S)-4-(tert-butyldimethylsiloxy)-3-(benzyloxy)-2-hydroxybutoxy)phenyl)ethanone 3 (Table 2)

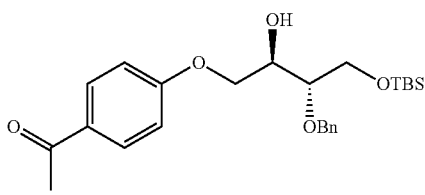 [SMILES: CC(=O)c1ccc(OC[C@@H](O)[C@H](CO[Si](C)(C)C(C)(C)C)OCc2ccccc2)cc1]

Yield: 98% white solid mp: 91-92° C.; IR (CHCl$_3$, cm$^{-1}$): 699.28, 775.75, 957.19, 1093.07, 1258.78, 1359.27, 1470.93, 1575.75, 1600.40, 1671.94, 2856.59, 2928.76, 3473.28; $^1$H NMR (200 MHz, CDCl$_3$) δ 0.09 (S, 6H), 0.92 (s, 9H), 2056 (s, 3H), 2.90 (sb 1H), 3.66 (m, 1H), 3.88 (dd, j=2.17 Hz, 2H), 4.14 (m, 3H), 4.68 (dd, J=11.62 Hz, 2H), 6.90 (m, 2H), 7.27 (m, 5H), 7.92 (m, 2H); $^{13}$C NMR (50 MHz, CDCl$_3$): −5.42, 18.28, 25.93, 26.33, 63.27, 69.20, 71.04, 72.81, 78.42, 114.26, 127.90, 128.00, 128.45, 130.57, 137.97, 162.63, 196.45; Anal. Calcd. for C$_{25}$H$_{36}$O$_5$Si requires C, 67.53; H, 8.16. found C, 67.49; H, 8.16.

20. Compound of methyl 4-((2R,3S)-4-(tert-butyldimethylsiloxy)-3-(benzyloxy)-2-hydroxybutoxy)benzoate 5 (Table 2)

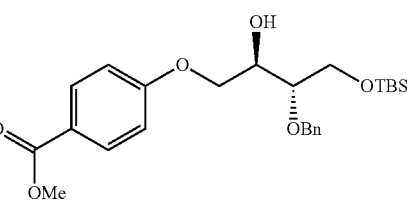

Yield: 81% colorless liquid; IR (CHCl$_3$, cm$^{-1}$): 771.58, 837.64, 1169.55, 1255.29, 1435.72, 1511.62, 1605.92, 1718.16, 2928.78, 3478.36; $^1$H NMR (200 MHz, CDCl$_3$) 80.09 (s, 6H), 0.91 (s, 9H), 2.94 (sb, 1H), 3.63 (m, 1H), 3.91 (m, 5H), 4.12 (m, 3H), 4.68 (dd, J=11.6 Hz, 2H), 6.92 (dt, J=2.81 Hz, 2H), 7.27 (m, 5H), 7.98 (dt, J=2.71 Hz, 2H); $^{13}$C NMR (50 HZ, CDCl$_3$): −5.40, 18.29, 25.94, 51.84, 63.28, 69.15, 70.94, 72.82, 78.51, 114.17, 122.81, 128.02, 128.44, 131.61, 138.0, 162.46, 166.70; Anal. Calcd. for C$_{25}$H$_{36}$O$_6$Si requires C, 65.19; H, 7.88. found C, 65.18; H, 7.86.

21. Compound of 4-((2R,3S)-4-(tert-butyldimethylsiloxy)-3-(benzyloxy)-2-hydroxybutoxy)benzonitrile 1 (Table 2)

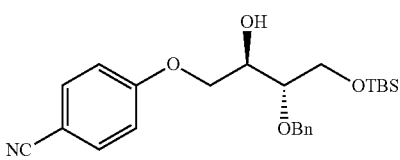 [SMILES: CC(C)(C)[Si](C)(C)OC[C@H](OCc1ccccc1)[C@H](O)COc1ccc(C#N)cc1]

Yield: 87% colorless solid, mp: 62-63° C.; IR (CHCl$_3$, cm$^{-1}$): 778.43, 835.46, 1096.18, 1172.50, 1258.45, 1302.46, 1454.96, 1508.86, 1605.60, 2224.99, 2856.83, 2883.40, 2929.04, 2953.53, 3474.10; $^1$H NMR (200 MHz, CDCl$_3$) δ 0.09 (s, 6H), 0.91 (s, 9H), 2.92 (m, 1H), 3.64 (m, 1H), 3.86 (s, 1H), 3.89 (d, J=Hz, 1H), 4.11 (m, 3H), 4.56 (d, J=HZ, 1H), 4.67 (d, J=Hz, 1H), 6.95 (dt, J=Hz, 2H), 7.27 (m, 5H), 7.59 (dt, J=2.65 Hz, 2H); $^{13}$C NMR (50 HZ, CDCl$_3$): −5.55, 18.13, 25.78, 62.97, 69.31, 72.59, 78.28, 104.04, 115.18, 118.83, 127.75, 127.8, 128.29, 133.74, 137.79, 161.97; Anal. Calcd. for C$_{24}$H$_{33}$NO$_4$Si requires C, 67.41; H, 7.78; N 3.28. found C, 67.42; H, 7.80.

22. Compound of 4-((2R,3S)-4-(tert-butyldimethylsiloxy)-3-(benzyloxy)-2-hydroxybutoxy)benzaldehyde 4 (Table 2)

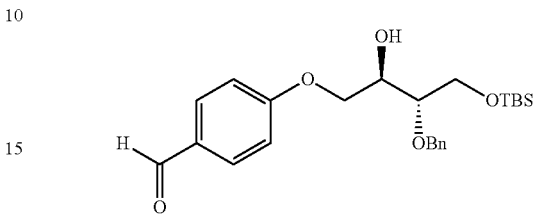

Yield: 75%; gum; IR (neat, cm$^{-1}$): 755, 834, 1097, 1256, 1462, 1509, 1600, 1693, 2928, 3454; $^1$H-NMR (200 MHz, CDCl$_3$): δ 0.09 (s, 6H), 0.92 (s, 9H), 2.95 (br s, 1H), 3.65 (m, 1H) 3.88 (m, 2H), 4.14 (m, 3H), 4.68 (dd, j=11.62 Hz, 2H), 7.00 (m, 2H), 7.84 (m, 2H), 9.88 (s, 1H); $^{13}$C-NMR (50 MHz, CDCl$_3$): δ −542, 18.27, 25.92, 63.21, 69.35, 71.04, 72.78, 78.32, 114.86, 128, 128.45, 130.16, 131.16, 131.94, 137.91, 163.74, 190.49; Anal. Calcd. for C$_{24}$H$_{34}$O$_5$Si: C, 66.94; H, 7.96; 0, 18.58; Si, 6.52. Found: C, 66.91; H, 7.95; O, 18.56; Si, 6.51%.

23. Compound of (2R,3S)-1-(2,4,5-trichlorophenoxy)-4-(tert-butyldimethylsiloxy)-3-(benzyloxy)butan-2-ol 6 (Table 2)

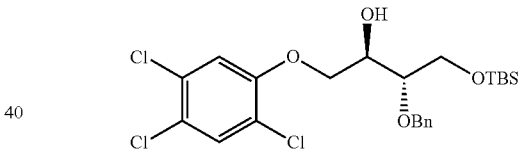

Yield: 78%; gum; IR (neat, cm$^{-1}$): 701, 763, 1050, 1261, 1454, 1492, 2104, 2935, 3034, 3416; $^1$H-NMR (200 MHz, CDCl3): δ 0.09 (s, 6H), 0.92 (s, 9H), 2.90 (s, 1H), 3.68 (m, 1H) 4.03 (m, 5H), 4.69 (m, 2H), 6.93 (s, 1H), 7.28 (m, 5H), 7.43 (s, 1H); $^{13}$C-NMR (50 MHz, CDCl3): δ −540, 18.30, 25.94, 63.42, 70.62, 70.89, 72.91, 78.23, 115.03, 122.101, 124.39, 127.90, 128.46, 130.80, 131.26, 137.97, 153.35; Anal. Calcd. for C$_{23}$H$_{31}$Cl$_3$O$_4$Si: C, 54.60; H, 6.18; Cl, 21.02; O, 12.65; Si, 5.55. Found: C, 54.58; H, 6.15; Cl, 21.01; O, 12.62; Si, 5.51;%.

24. Compound of (2R,3S)-4-(tert-butyldimethylsiloxy)-1-(4-nitrophenoxy)-3-(benzyloxy)butan-2-ol 2 (Table 2)

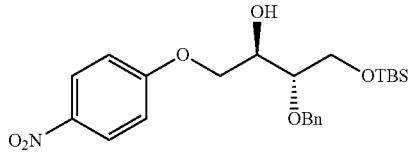 [SMILES: CC(C)(C)[Si](C)(C)OC[C@H](OCc1ccccc1)[C@H](O)COc1ccc([N+](=O)[O-])cc1]

Yield: 89%; colorless liquid; IR (neat, cm$^{-1}$): 752, 778, 1111, 1263, 1340, 1517, 1593, 2856, 2928, 3472; $^1$H-NMR (200 MHz, CDCl$_3$): δ 0.10 (s, 6H), 0.92 (s, 9H), 2.97 (br s, 1H), 3.62 (m, 1H) 3.90 (m, 2H), 4.15 (m, 3H), 4.68 (dd, j=11.68 Hz, 2H), 6.94 (m, 2H), 7.29 (m, 5H), 8.20 (m, 2H); $^{13}$C-NMR (50 MHz, CDCl$_3$): δ −548, 18.22, 25.86, 63.05, 69.80, 71.02, 72.68, 78.11, 114.49, 125.77, 127.96, 128.42, 137.78, 141.61, 163.70; Anal. Calcd. for C$_{23}$H$_{33}$NO$_6$Si: C, 61.72; H, 7.43; N, 3013; 0, 21.45; Si, 6.27. Found: C, 61.70; H, 7.42; N, 3.13; O, 21.44; Si, 6.25;%.

25. Compound of 1-(4-((2R,3R)-3-(benzyloxy)-2-hydroxy-3-phenylpropoxy)phenyl)ethanone 1 (Table 4)

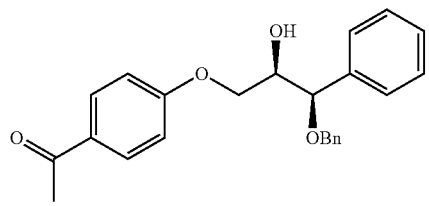 [SMILES: CC(=O)c1ccc(OC[C@@H](O)[C@H](OCc2ccccc2)c2ccccc2)cc1]

Yield: 89%; gum; IR (neat, cm$^{-1}$): 701, 755, 1065, 1255, 1358, 1454, 1599, 1673, 3453; $^1$H-NMR (200 MHz, CDCl$_3$): δ 2.54 (s, 3H), 3.04 (br s, 1H), 3.80 (m, 1H) 4.05 (m, 2H), 4.51 (m, 3H), 6.84 (m, 2H), 7.34 (m, 9H), 7.86 (m, 2H); $^{13}$C-NMR (50 MHz, CDCl$_3$): δ 26.23, 68.00, 70.86, 73.95, 81.48, 114.17, 127.48, 127.89, 127.98, 128.45, 128.56, 128.75, 130.46, 137.50, 137.82, 162.42, 196.27; Anal. Calcd. for C$_{24}$H$_{24}$O$_4$: C, 76.57; H, 6.43; O, 17.00%. Found: C, 76.56; H, 6.41; O, 17.01%.

The invention claimed is:

1. A single step process for the synthesis of α-Aryloxy-α'-Azido/Alkoxy alcohols of general formula A with two stereocenters by phenolic kinetic resolution,

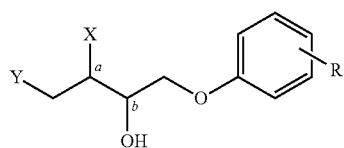
(formula A)

wherein X is selected from N$_3$ and O-benzyl (OBn);
'R' is selected independently from hydrogen, alkyl (C$_1$-C$_5$), alkenyls (C$_2$-C$_6$), alkynyls (C$_2$-C$_6$), aryl, alkoxy, cyano, halo, nitro, —C(O)—R$_1$, —CO$_2$R$_2$, hydroxyl, —NH(R$_3$), cycloalkyl, cycloalkenyl, thiols, thiocarbonyl, sulfonyl or a heterocycle(C3-C$_5$), where R$_1$, R$_2$ and R$_3$ represent hydrogen, alkyl(C$_1$-C$_5$);
Y denotes O-tert-butyldimethylsilyl (OTBS) or phenyl; and
'a' and 'b' denote syn or anti position;
wherein the said process comprising the steps of:
(a) adding racemic epoxide of formula (1),

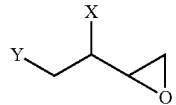
Formula 1 to phenol of formula (2)

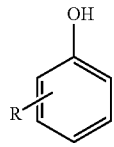
Formula 2 wherein, X, Y and R are as defined above,
at room temperature ranging between 25-35° C. to preformed (salen) Co (III) catalyst of formula 3,

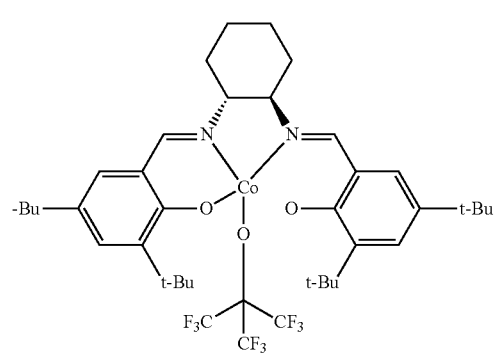
Formula 3

(R,R)-Co salen complex 3 followed by addition of tertiary butyl methyl ether, stirring and adding pyridinium p-toluene sulfonate, filtering, concentrating, followed by purifying to obtain the α-Aryloxy-α'-Azido/Alkoxy alcohols of general formula A.

2. The process according to claim 1, wherein the anti α-Aryloxy-α'-Azido/Alkoxy alcohols, is represented by formula 4;

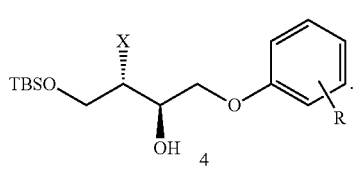
Formula 4

4a: X = N$_3$, (2S, 3S)
4b: X = OBn (2R, 3S)

3. The process according to claim 1, wherein the syn α-Aryloxy-α'-Azido/Alkoxy alcohols is, represented by formula 7;

Formula 7

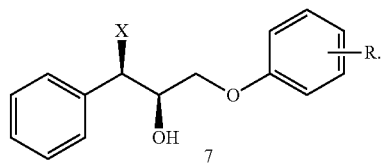

7a: X = N₃, (2S, 3S)
7b: X = OBn (2R, 3S)

4. The process according to claims 2 and 3, wherein the α-Aryloxy-α'-Azido/Alkoxy alcohols of formula 4 and 7 comprises:

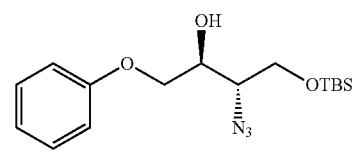

(2S,3S)-3-azido-4-(tert-butyl-dimethylsiloxy)-1-phenoxybutan-2-ol

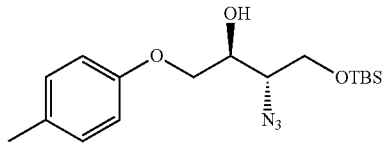

(2S,3S)-1-(p-tolyloxy)-3-azido-4-(tert-butyl-dimethyl siloxy)butan-2-ol

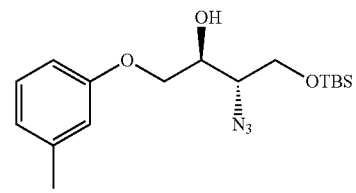

(2S,3S)-1-(m-tolyloxy)-3-azido-4-(tert-butyl-dimethyl siloxy)butan-2-ol

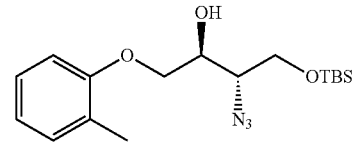

(2S,3S)-1-(o-tolyloxy)-3-azido-4-(tert-butyl-dimethyl siloxy)butan-2-ol

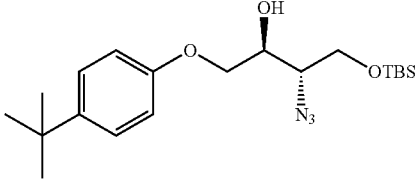

(2S,3S)-1-(4-tert-butylphenoxy)-3-azido-4-(tert-butyl-dimethylsiloxy)butan-2-ol

-continued

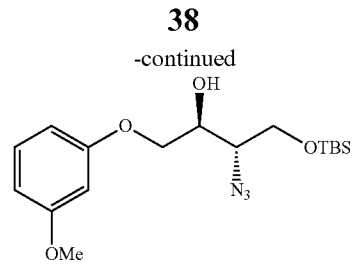

(2S,3S)-1-(3-methoxyphenoxy)-3-azido-4-(tert-butyl-dimethylsiloxy)butan-2-ol

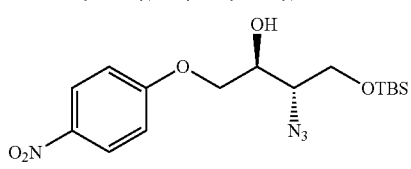

4-((2S,3S)-(3-azido-4-(tert-butyl-dimethyl siloxy)-2-hydroxybutoxy)benzonitrile

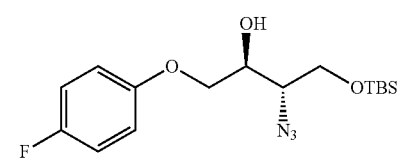

(2S,3S)-1-(4-nitrophenoxy)-3-azido-4-(tert-butyl-dimethyl siloxy)butan-2-ol

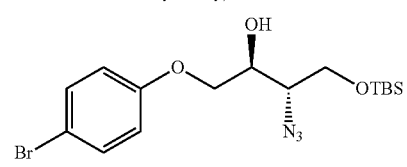

(2S,3S)-1-(4-fluorophenoxy)-3-azido-4-(tert-butyl-dimethylsiloxy)butan-2-ol

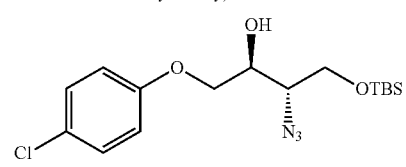

(2S,3S)-1-(4-bromophenoxy)-3-azido-4-(tert-butyl-dimethyl siloxy) butan-2-ol

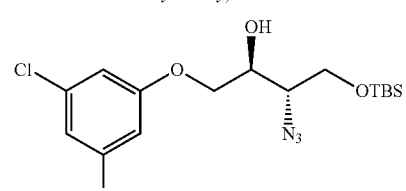

(2S,3S)-1-(4-chlorophenoxy)-3-azido-4-(tert-butyl-dimethyl siloxy)butan-2-ol (2S,3S)-1-(3,5-dichlorophenoxy)-3-azido-4-tert-butyl-dimethylsiloxy)butan-2-ol

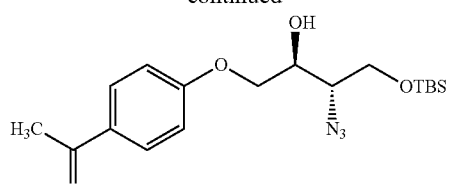

1-(4-(2S,3S)-(3-azido-4-(tert-butyl-dimethyl siloxy)-2-hydroxybutoxy)phenyl)ethanone

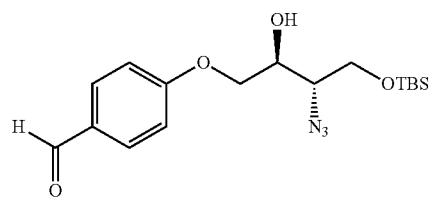

4-((2S,3S)-(3-azido-4-tert-butyl-dimethyl siloxy)-2-hydroxybutoxy)benzaldehyde

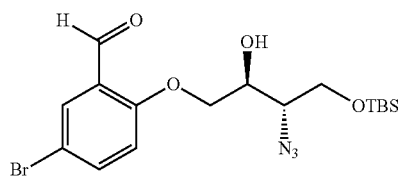

2-(2S,3S)-(3-azido-4-(tert-butyl-dimethyl siloxy)-2-hydroxybutoxy)-5-bromobenzaldehyde

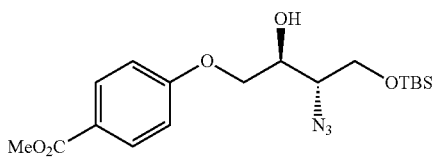

Methyl-4-((2S,3S)-(3-azido-4-(tert-butyl-dimethylsiloxy)-2-hydroxybutoxy)benzoate

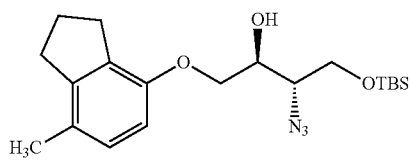 [SMILES: Cc1ccc(OC[C@@H](O)[C@H](CO[Si](C)(C)C(C)(C)C)N=[N+]=[N-])c2c1CCC2]

(2S,3S)-1-(2,3-dihydro-4-methyl-1H-inden-7-yloxy)-3-azido-4-(tert-butyl-dimethylsiloxy)butan-2-ol

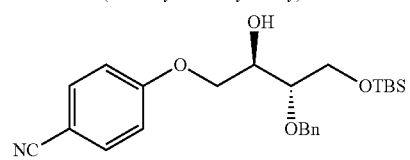

4-((2R,3S)-4-(tert-butyl dimethylsiloxy)-3-(benzyloxy)-2-hydroxybutoxy)benzonitrile

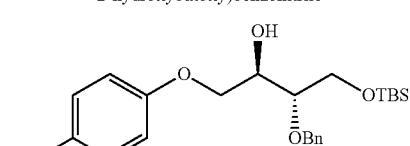

(2R,3S)-4-(tert-butyl dimethylsiloxy)-1-(4-nitrophenoxy)-3-(benzyloxy)butan-2-ol

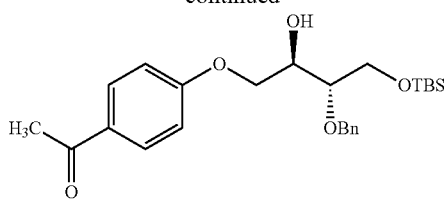

1-(4-((2R,3S)-4-(tert-butyldimethylsiloxy)-3-(benzyloxy)-2-hydroxybutoxy)phenyl)ethanone

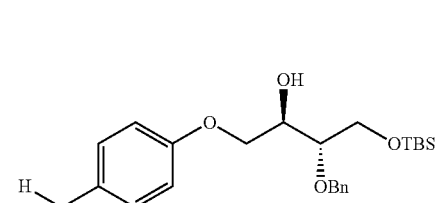

4-((2R,3S)-4-(tert-butyldimethylsiloxy)-3-(benzyloxy)-2-hydroxybutoxy)benzaldehyde

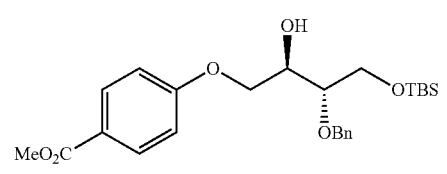

methyl 4-((2R,3S)-4-(tert-butyl dimethylsiloxy)-3-(benzyloxy)-2-hydroxybutoxy)benzoate

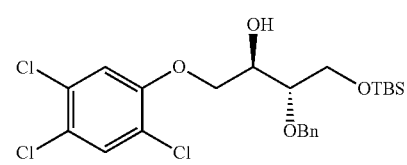

(2R,3S)-1-(2,4,5-trichlorophenoxy)-4-(tert-butyldimethylsiloxy)-3-(benzyloxy)butan-2-ol

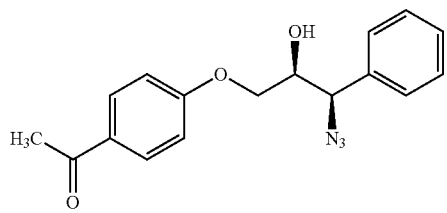

1-(4-((2S,3R)-3-azido-2-hydroxy-3-phenylpropoxy)phenyl)ethanone

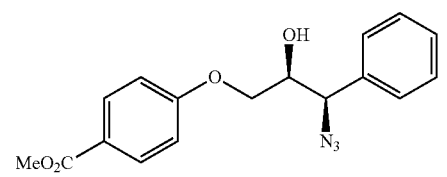

methyl 4-((2S,3R)-3-azido-2-hydroxy-3-phenylpropoxy)-benzoate

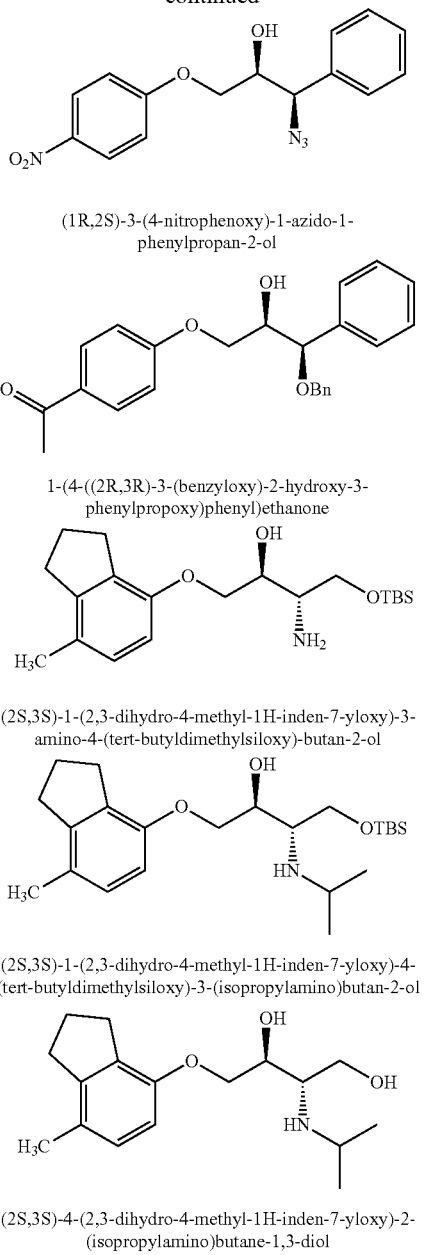

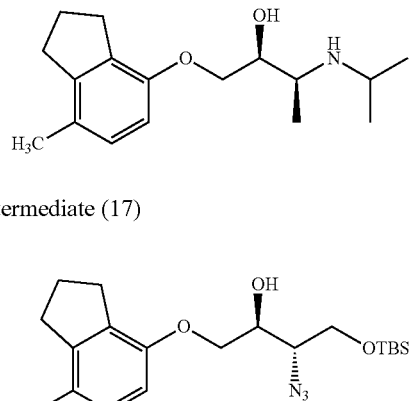

5. The process as claimed in claim 1 wherein the yield of α-Aryloxy-α'-Azido/Alkoxy alcohols of general formula A is in the range of 35-98%.

6. The process as claimed in claim 1 wherein enantiomeric excess (ee) % of α-Aryloxy-α'-Azido/Alkoxy alcohols of general formula A is in the range of 94-99%.

7. Asymmetric synthesis of antihypertensive agent ICI118, 551((2S,3S)-1-(2,3-dihydro-4-methyl-1H-inden-7-yloxy)-3-(isopropylamino)butan-2-ol)

from intermediate (17)

(2S,3S)-1-(2,3-dihydro-4-methyl-1H-inden-7-yloxy)-3-azido-4-(tert-butyl-dimethyl siloxy)butan-2-ol (17)
  comprising;
    i. reducing intermediate (17) obtained from the process of claim 1 in the presence Of Pd/C in lower alcohol;
    ii. protecting the amino group with isopropyl chloride in presence of a base and halogenated hydrocarbon as solvent;
    iii. deprotecting the terminal alcohol group with CSA (2S, 3S)-4-(2,3-dihydro-4-methyl-1H-inden-7-yloxy)-2-(isopropylamino)butane-1,3-diol) in lower alcohol at room temperature ranging between 25-35° C.;
    iv. reacting the product of step (iii) with p-TsCl (p-Toluenesulfonyl chloride) in presence of a base and halogenated hydrocarbon as solvent at temperature ranging between 0° C. to 25° C.; and
    v. reducing the compound of step (iv) with LiAlH$_4$ in THF at reflux to obtain antihypertensive agent ICI118,.

8. A process as claimed in claim 7, wherein lower alcohol used in step (i) and (iii) is selected from the group consisting of methanol or ethanol.

9. A process as claimed in claim 7, wherein base used in step (ii) and (iv) is selected from the group consisting of ethylamine, triethylamine or pyridine.

10. A process as claimed in claim 7, wherein halogenated solvent used in step (ii) and (iv) is selected from the group consisting of chloroform, carbon tetrachloride or Dichloromethane.

* * * * *